United States Patent
Mewissen et al.

(10) Patent No.: US 6,633,049 B2
(45) Date of Patent: Oct. 14, 2003

(54) APPARATUS FOR RADIATION TREATMENT WITH A HOMOGENEOUS UVB DISTRIBUTION

(75) Inventors: Jan Alfons Catharina Mewissen, Drachten (NL); Thomas Nicolaas Maria Bernards, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 10/023,164

(22) Filed: Dec. 18, 2001

(65) Prior Publication Data

US 2002/0117638 A1 Aug. 29, 2002

(30) Foreign Application Priority Data

Dec. 22, 2000 (EP) .............................. 00204801

(51) Int. Cl.⁷ .............................. G21G 5/00; G01T 1/20; G01J 1/42
(52) U.S. Cl. ............... 250/504 R; 250/492.1; 250/365; 250/372
(58) Field of Search ................ 250/492.1, 504 R, 250/365, 372

(56) References Cited

U.S. PATENT DOCUMENTS

| | | | |
|---|---|---|---|
| 4,323,810 A | * 4/1982 | Horstmann | 313/24 |
| 5,347,342 A | * 9/1994 | Ehr | 355/113 |
| 5,387,798 A | * 2/1995 | Funakoshi et al. | 250/474.1 |
| 5,387,801 A | * 2/1995 | Gonzalez et al. | 250/504 R |
| 5,737,065 A | * 4/1998 | Hansen | 355/113 |
| 6,201,250 B1 | * 3/2001 | Morlock | 250/372 |
| 6,464,714 B1 | * 10/2002 | Mewissen et al. | 607/90 |
| 6,465,799 B1 | * 10/2002 | Kimble et al. | 250/504 R |

* cited by examiner

*Primary Examiner*—John R. Lee
*Assistant Examiner*—Mary El-Shammaa
(74) *Attorney, Agent, or Firm*—Ernestine C. Barlett

(57) ABSTRACT

An apparatus (1) for treatment with radiation for personal care, comprising a housing (2) provided with a UV source (3) and a wall (4) made of UV-transparent material which covers the housing (2) and which has a central area (7) and side areas (8) adjoining the central area (7). The wall (4) has a lower transmission to radiation with a wavelength <320 nm near the central area (7) than near the side areas (8). Thus the effective radiation energy of radiation with a wavelength <320 nm reaching the side portions of the irradiation plane (9) approximates a value of 0.14 W/m² (European standard EN 60335-2-27), while the effective radiation energy of radiation with a wavelength <320 nm reaching the central portion of the irradiation plane (9) also approximates this value. This results in a practically uniform distribution of effective radiation energy of radiation with a wavelength <320 nm over the radiation surface (9) as a whole. A tanning result which is as uniform as possible is thus achieved in a time period which is as short as possible.

9 Claims, 3 Drawing Sheets

APPARATUS FOR RADIATION TREATMENT WITH A HOMOGENEOUS UVB DISTRIBUTION

BACKGROUND OF THE INVENTION

The invention relates to an apparatus for radiation treatment for personal care, comprising a housing in which a UV source is present and a wall made from a UV-transmitting material which covers the housing, said wall having a central area and side areas adjoining the central area.

Such an apparatus for radiation treatment for personal care is generally known. If the apparatus is used as a suntanning apparatus, a user is present in an irradiation plane of the UV source extending in a longitudinal direction so as to achieve a tanning of the skin. The UV source used for this produces a comparatively large quantity of effective radiation with a wavelength in the range <320 nm (UVB), which radiation is mainly responsible for tanning of the skin, and a comparatively small quantity of effective radiation with a wavelength in the range from 320 to 400 nm (UVA). The UV-transmitting wall has for its object to filter out a large quantity of radiation with a wavelength <320 nm, such that the value of the effective radiation energy thereof does not exceed the value of 0.14 W/m$^2$ (European standard EN 60335-2-27) in the irradiation plane. The natural distribution of the resulting effective radiation energy over the longitudinal direction of the irradiation plane is such that a substantially higher effective radiation energy is present in the central area of the irradiation plane than in the side areas of the irradiation plane. The effective radiation energy in the side areas of the irradiation plane is approximately 50% of the effective radiation energy in the central area of the irradiation plane during operation of the known apparatus. To obtain an even tanning, however, a homogeneous distribution of the effective radiation energy of the UV source over the longitudinal direction of the irradiation plane is desirable. A disadvantage of the known apparatus, therefore, is that an optimum homogeneous suntanning cannot be achieved with the apparatus.

A homogeneous distribution of the effective radiation energy of the UV source over the longitudinal direction of the irradiation plane can be realized in principle by means of specific optical properties of a reflector system adjacent the UV source, but this brings with it the consequence that the total radiation energy in the irradiation plane is comparatively low. It is true that such a reflector system spreads the radiation such that an effective radiation energy evenly distributed over the irradiation plane is achieved. At the same time, however, a substantial portion of the effective radiation energy falls outside the irradiation plane in this manner, which implies a loss of effective radiation energy. This means that a comparatively long suntanning time is required for obtaining an even tanning, which is not desirable.

SUMMARY OF THE INVENTION

It is an object of the invention to provide an apparatus of the kind mentioned in the opening paragraph with which a tanning of the skin which is as even as possible can be realized in a time period which is as short as possible.

The above object is achieved with an apparatus according to the invention which is characterized in that the wall has a lower transmission to radiation with a wavelength <320 nm adjacent the central area than adjacent the side areas. The comparatively large quantity of radiation having a wavelength <320 nm radiated by the UV source is better transmitted by the wall adjacent the side areas of the wall than adjacent the central area of the wall in this manner during operation of the apparatus. The transmission is such here that the effective radiation energy of radiation having a wavelength <320 nm and incident on the lateral portions of the irradiation plane approximates the value of 0.14 W/m$^2$ (European standard EN 60335-2-27), while the effective radiation energy of radiation having a wavelength <320 nm and incident on the central portion of the irradiation plane also approximates this value. This results in a distribution of effective radiation energy of radiation having a wavelength <320 nm which is substantially homogeneous viewed over the entire irradiation plane. An even tanning of the skin of a user of the apparatus can thus be realized without a long treatment period of the user in the irradiation plane being necessary.

An embodiment of an apparatus according to the invention is characterized in that the wall has a greater thickness adjacent the central area than adjacent the side areas. Since the wall is thicker adjacent the central area than adjacent the side areas, the wall has a lower transmission to radiation with a wavelength <320 nm adjacent the central area than adjacent the side areas. A substantially homogeneous distribution of effective radiation energy of radiation having a wavelength <320 nm over the irradiation plane during use is thus realized in a manner which is constructionally comparatively simple.

It is favorable in this respect if the wall comprises a layer in the form of a coating which has a greater thickness adjacent the central area than adjacent the side areas. A coating can be provided on the wall with a variable thickness in a comparatively simple manner in mass manufacture.

A further embodiment of an apparatus according to the invention is characterized in that the wall is manufactured from a first material having a comparatively high transmissivity to radiation with a wavelength <320 nm, and a second material is provided adjacent the central area, which second material has a comparatively low transmissivity to radiation with a wavelength <320 nm. As a result, the wall transmits a greater proportion of radiation having a wavelength <320 nm at the side areas, whereas in the central area, where the second material is present, less radiation having a wavelength <320 nm is transmitted. The transmission is such in this manner that the effective radiation energy of radiation with a wavelength <320 nm reaching the side portions of the irradiation plane approximates the value of 0.14 W/m$^2$ (European standard EN 60335-2-27), while the effective radiation energy of radiation with a wavelength <320 nm reaching the central portion of the irradiation plane also approximates this value. This results in a substantially homogeneous distribution of effective radiation energy of radiation with a wavelength <320 nm over the irradiation plane, so that an even tanning of the skin of a user of the apparatus can be realized without a long treatment time of the user in the irradiation plane being necessary.

It is advantageous here if the second material has a comparatively high transmissivity to radiation with a wavelength in the range from 320 to 400 nm. The UV source produces a small quantity of radiation in this range, which quantity, if fully transmitted by the wall, poses no risk to the user. Since the second material has a comparatively high transmissivity to radiation with a wavelength in the range from 320 to 400 nm, this radiation is transmitted to the central portion of the irradiation plane to a substantial degree, which contributes to an optimum utilization of this radiation.

It is furthermore advantageous if the second material is provided in a predetermined pattern. In that case the material can be provided on the wall in a comparatively simple manner during manufacture.

A further embodiment of an apparatus according to the invention is characterized in that intermediate areas are present between the central area and the side areas, in which intermediate areas the wall has a transmission to radiation with a wavelength <320 nm which lies between the transmission adjacent the central area and the transmission adjacent the side areas. The intermediate areas contribute further to the realization of a substantially homogeneous distribution of effective radiation energy of radiation with a wavelength <320 nm over the irradiation plane.

A further embodiment of an apparatus according to the invention is characterized in that the housing has a base wall which extends substantially parallel to the UV-transmitting wall, and the housing has at least one reflecting side wall which extends from the base wall along the UV source at an angle to said base wall, and the reflecting side wall at a side facing the UV source comprises a material which has a comparatively low reflectivity to radiation with a wavelength <320 nm. In this manner, only a small quantity of radiation with a wavelength <320 nm is reflected by the side wall to the central area of the wall, so that the resulting effective radiation energy of this radiation in the central portion of the irradiation plane will be limited. This also benefits the homogeneous distribution of said effective radiation energy over the irradiation plane.

It is advantageous in this connection if said material has a comparatively high reflectivity to radiation with a wavelength in the range from 320 to 400 nm. Radiation with a wavelength in the range from 320 to 400 nm is thus reflected to a high degree towards the central area of the wall, which contributes to an optimum utilization of this radiation, in view of the small quantity of radiation produced by the UV source in this range.

BRIEF DESCRIPTION OF THE DRAWINGS

The apparatus according to the invention will be explained in more detail below with reference to the drawing, in which.

DETAILED DESCRIPTION OF THE INVENTION

Figure 1:
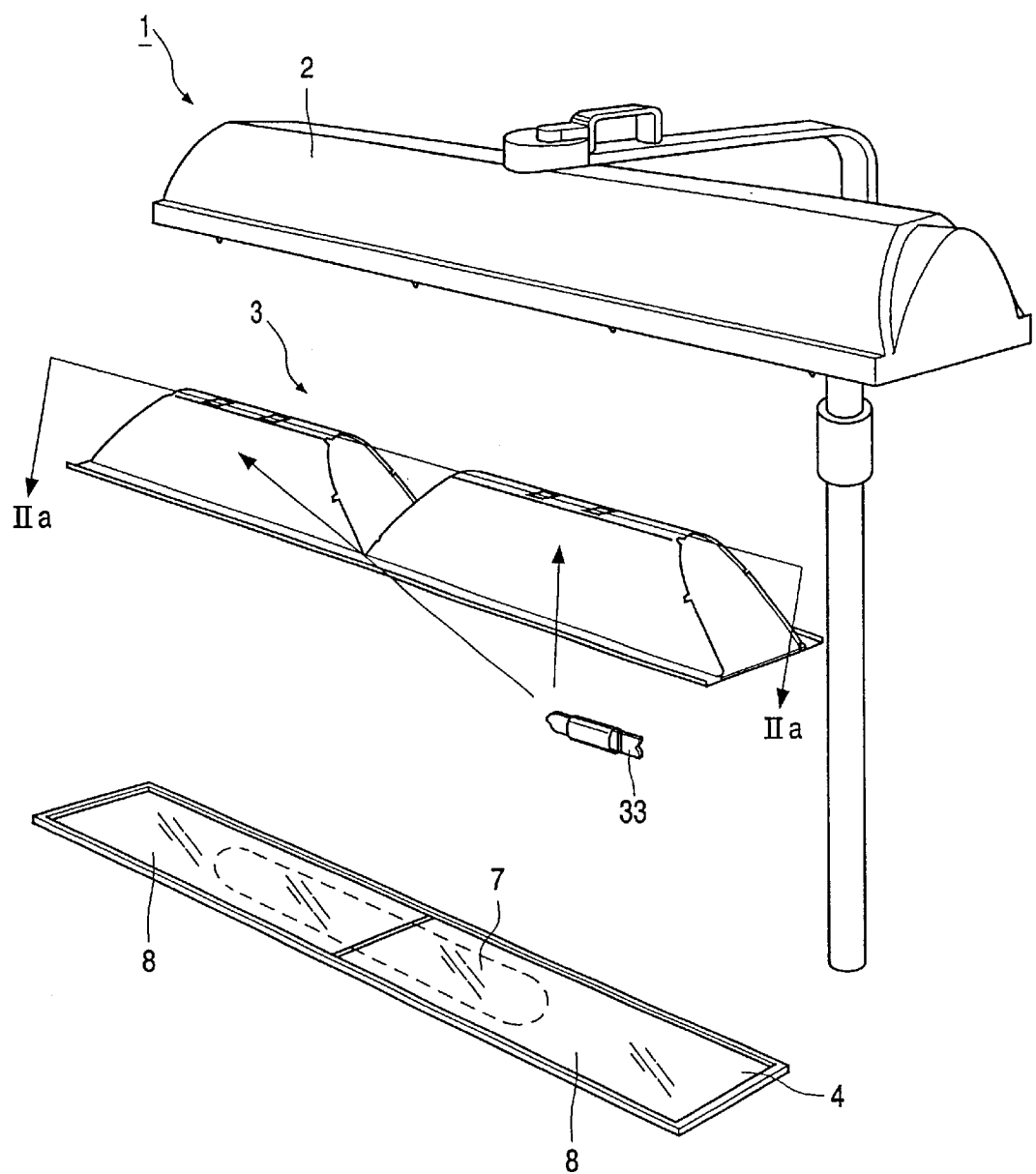
FIG. 1 shows a first embodiment of the apparatus for radiation treatment for personal care according to the invention in exploded view.
Figure 2A:
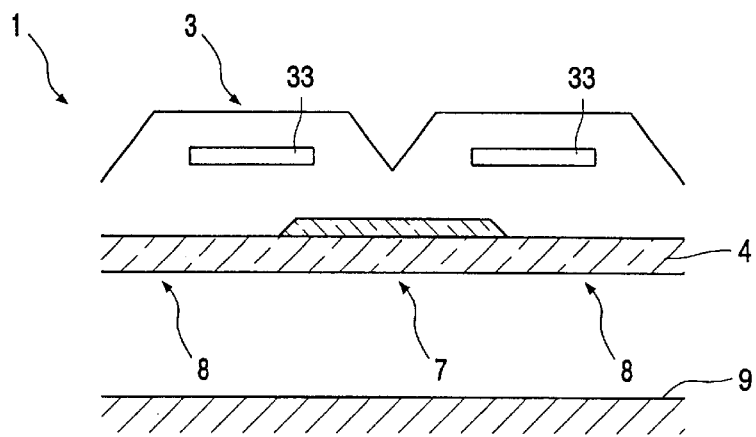
FIG. 2a is a cross-sectional view of the apparatus taken on the line IIa—IIa in FIG. 1.

FIG. 1 shows a first embodiment of the apparatus 1 for radiation treatment for personal care according to the invention, with a housing 2 in which a UV source 3 is present which in this embodiment comprises two compact UV lamps 33. The apparatus 1 further comprises a wall 4 manufactured from a light-transmitting material and closing off the housing 2. In this embodiment, the wall 4 is made from an inorganic glass, but the wall may alternatively be made from any other known type of UV-transmitting material. The wall 4 has a central area 7 and side areas 8 adjoining the central area, as viewed in longitudinal direction. The wall 4 has a lower transmission to radiation having a wavelength <320 nm adjacent the central area 7 than adjacent the side areas 8. This is realized in this embodiment in that the wall has a greater thickness adjacent the central area than adjacent the side areas, as is apparent from FIG. 2a. It is advantageous if this greater thickness adjacent the central area is realized by means of a coating 21 on the wall, which coating is provided in a greater number of layers adjacent the central area 7 than adjacent the side areas 8. The coating in this embodiment comprises a sol-gel material, but the coating may alternatively comprise any other known type of material. The radiation originating from the UV source 3 is thus better transmitted adjacent the side areas 8 of the wall than adjacent the central area 7 of the wall 4. As a result, a distribution of effective radiation energy resulting from radiation with a wavelength <320 nm over an irradiation plane 9 is realized as indicated with the curve UVBinv. in FIG. 2b. The value of the effective radiation energy is plotted on the vertical axis in FIG. 2b, and the longitudinal direction of the irradiation plane 9 is plotted on the horizontal axis. Compared with the curve UVBnorm, which indicates the distribution of effective radiation energy resulting from radiation with a wavelength <320 nm in a known apparatus, it is apparent that the distribution realized over the longitudinal direction of the irradiation plane 9 by means of the apparatus according to the invention is substantially homogeneous. The problem of an uneven distribution of the effective radiation energy solved by the invention arises in particular in the longitudinal direction of the irradiation plane, which is why the distribution in lateral direction is not pictured here. It is furthermore visible in FIG. 2b that the distribution UVTotinv. of the total effective radiation energy resulting from radiation from the UV source with a wavelength <320 nm and with a wavelength in the range from 320 to 400 nm taken together is also more homogeneous in an apparatus according to the invention than the corresponding distribution UVTotnorm realized in a known apparatus.

Figure 3A:
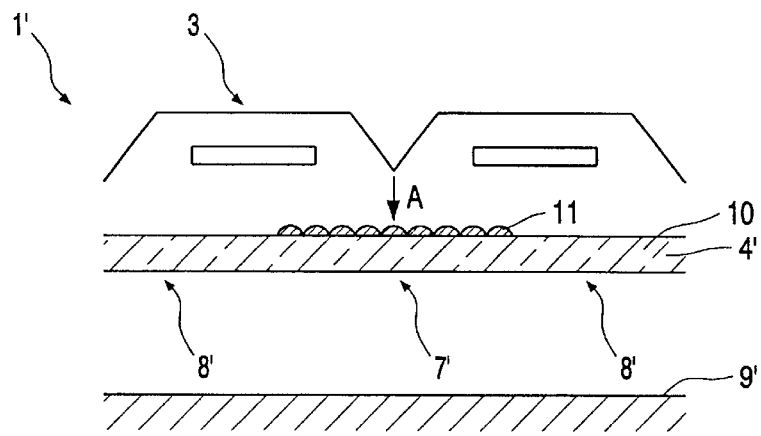
FIG. 3b shows a filter of the apparatus of FIG. 3a viewed from a direction A in FIG. 3a, FIG. 4 is a cross-sectional view of a third embodiment of an apparatus for radiation treatment for personal care according to the invention.

FIG. 3a shows a second embodiment of an apparatus 1' for radiation treatment for personal care according to the invention. In this embodiment, the wall 4' is manufactured from a first material 10 with a comparatively high transmissivity to radiation having a wavelength <320 nm, and a second material 11 is provided adjacent the central area having a comparatively low transmissivity to radiation with a wavelength <320 nm. The first material in this embodiment comprises inorganic glass, but the first material may alternatively comprise some other known type of material with a comparatively high transmissivity to radiation with a wavelength <320 nm. The second material in this embodiment comprises a sol-gel material, but the second material may alternatively comprise some other known types of material with a comparatively low transmissivity to radiation with a wavelength <320 nm.

Figure 2B:
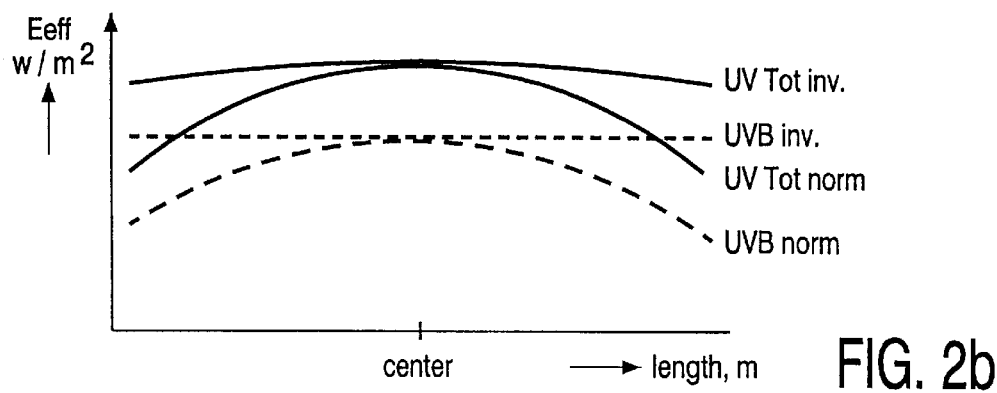
FIG. 2b is a graph showing a distribution of effective radiation energy of only radiation with a wavelength <320 nm over an irradiation plane, and also of this radiation in combination with radiation having a wavelength in the range from 320 to 400 nm, during operation of a known apparatus and during operation of the apparatus of FIG. 2a, FIG. 3a shows a second embodiment of an apparatus for radiation treatment for personal care according to the invention in cross-section.

The distribution of effective radiation energy over an irradiation plane in this embodiment approximates the distribution as pictured in the graph of FIG. 2b. It is furthermore advantageous if the material 11 has not only a comparatively low transmissivity to radiation with a wavelength <320 nm but also a comparatively high transmissivity to radiation with a wavelength in the range from 320 to 400 nm. The UV source 3 produces a small quantity of radiation in this range, which quantity if transmitted fully by the wall 4' will not be of any risk to the user. Since the second material 11 has a comparatively high transmissivity to radiation with a wavelength in the range from 320 to 400 nm, this radiation is transmitted for a major portion to the central portion of the irradiation plane 9. The comparatively small quantity of radiation produced by the UV source in this range is thus optimally utilized.

Figure 3B:
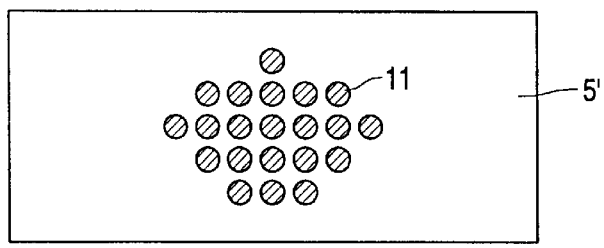

FIG. 3b shows the wall 4' viewed from a direction A in FIG. 3a. It is apparent here that the second material 11 is provided in a predetermined pattern of dots. It is noted that the shape of the material elements to be provided and the configuration in which this is done may be freely chosen in dependence on the desired embodiment of the apparatus for radiation treatment. It is also possible for the second material 11 to be provided on the wall 4' in shapes other than in dots, and in configurations other than the pattern shown in FIG. 3b.

Figure 4:
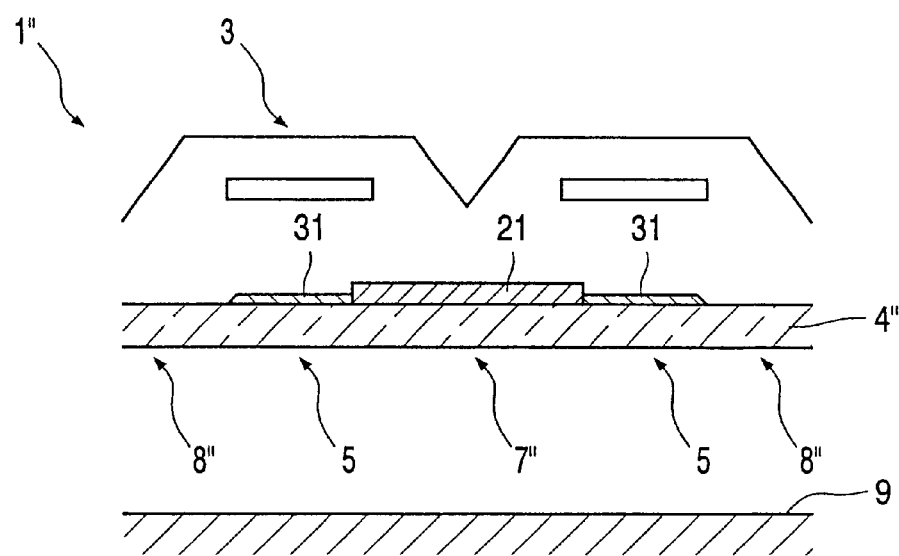

FIG. 4 shows a third embodiment of an apparatus 1" for radiation treatment for personal care according to the invention, in which intermediate areas 5 are present between the central area 7" and the side areas 8", in which areas 5 the wall 4" has a transmission to radiation with a wavelength <320 nm which lies between the transmission of the central area 7" and the transmission of the side areas 8". In this embodiment, the wall 4" comprises not only the coating 21, which is provided in a number of layers adjacent the central area as described with reference to FIG. 2a, but also further coating layers 31 provided adjacent to the intermediate areas 5 in a smaller number than the coating adjacent the central area. The wall 4" thus has a transmission to radiation with a wavelength <320 adjacent the intermediate areas 5 which lies between the transmission of the central area 7" and that of the side areas 8". The intermediate areas 5 thus contribute further to the realization of a substantially homogeneous distribution of effective radiation energy of radiation having a wavelength <320 nm over the irradiation plane. It is noted that the transmission of the intermediate areas may be realized in alternative manners such as, for example, by means of a further material which is provided adjacent the intermediate areas in the embodiment as described with reference to FIG. 3a.

Figure 5:
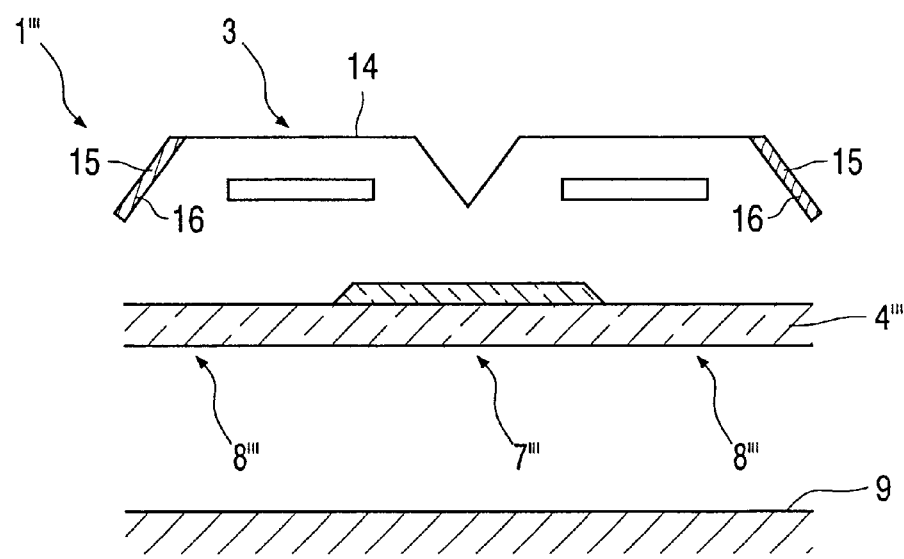
FIG. 5 is a cross-sectional view of a fourth embodiment of an apparatus for radiation treatment for personal care according to the invention.

FIG. 5 shows a fourth embodiment of an apparatus 1'" for radiation treatment for personal care according to the invention in which the housing 2 has a base wall 14 which extends substantially parallel to the UV-transmitting wall 4, which housing has at least one, in this embodiment two reflecting side walls 15 which extend from the base wall 14 but alongside the UV source 3 at an angle to said base wall. The reflecting side wall 15 comprises a material which has a comparatively low reflectivity for radiation with a wavelength <320 nm at a side facing the UV source. In this embodiment, this material 16 comprises an aluminum alloy, but the material may alternatively comprise any other known type of material with a comparatively low reflectivity to radiation with a wavelength <320 nm. This radiation is thus reflected towards the central portion of the irradiation plane to a low degree only. Furthermore, the wall 4'" has a lower transmission to radiation with a wavelength <320 nm adjacent the central area 7'" than adjacent the side areas 8'", which is realized in this embodiment in that the wall 4'" has a coating of greater thickness adjacent the central area 7'" than adjacent the side areas 8'". It is noted that the lower transmission adjacent the central area 7'" of the wall 4'" may be realized in alternative ways, for example as described for the second embodiment of the apparatus according to the invention. The combination of the wall 4'" with the reflecting side wall 15 comprising the material 16 of comparatively low reflectivity to radiation with a wavelength <320 nm contributes to an even more homogeneous distribution of the effective radiation energy over the entire irradiation plane. It is advantageous here, furthermore, if said material 16 has a comparatively high reflectivity to radiation with a wavelength in the range from 320 to 400 nm, so that the radiation in this range is optimally utilized.

It is noted that an apparatus for radiation treatment for personal care according to the invention also relates to types of such apparatuses other than the apparatus pictured in FIG. 1 such as, for example, a suntanning couch with a collapsible housing.

It is further noted that besides the embodiments mentioned above alternative embodiments are equally possible, in which the wall adjacent the central area has a lower transmission to radiation with a wavelength <320 nm than adjacent the side areas such as, for example, an embodiment in which the UV-transmitting wall is built up from materials with a varying transmissivity to radiation with a wavelength <320 nm.

What is claimed is:

1. An apparatus (1) for radiation treatment for personal care, comprising
   a housing (2) in which a UV source (3) is present; and
   a wall (4) made from a UV-transmitting material which covers the housing (2), said wall having a central area (7) and side areas (8) adjoining the central area,
   characterized in that the wall (4) has a lower transmission to radiation with a wavelength <320 nm adjacent the central area (7) than adjacent the side areas (8).

2. An apparatus as claimed in claim 1, characterized in that the wall (4) has a greater thickness adjacent the central area (7) than adjacent the side areas (8).

3. An apparatus as claimed in claim 2, characterized in that the wall (4) comprises a layer in the form of a coating which has a greater thickness adjacent the central area (7) than adjacent the side areas (8).

4. An apparatus as claimed in claim 1, characterized in that the wall (4) is manufactured from a first material (10) having a comparatively high transmissivity to radiation with a wavelength <320 nm, and a second material (11) is provided adjacent the central area (7), which material (11) has a comparatively low transmissivity to radiation with a wavelength <320 nm.

5. An apparatus as claimed in claim 4, characterized in that the second material (11) has a comparatively high transmissivity to radiation with a wavelength in the range from 320 to 400 nm.

6. An apparatus as claimed in claim 5, characterized in that the second material (11) is provided in a predetermined pattern.

7. An apparatus as claimed in claim 1, characterized in that intermediate areas (5) are present between the central area (7) and the side areas (8), in which intermediate areas the wall (4) has a transmission to radiation with a wavelength <320 nm which lies between the transmission adjacent the central area (7) and the transmission adjacent the side areas (8).

8. An apparatus as claimed in claim 1, characterized in that the housing (2) has a base wall (14) which extends substantially parallel to the UV-transmitting wall (4), and the housing has at least one reflecting side wall (15) which extends from the base wall (14) along the UV source (3) at an angle to said base wall (14), and the reflecting side wall (15) at a side facing the UV source (3) comprises a material (16) which has a comparatively low reflectivity to radiation with a wavelength <320 nm.

9. An apparatus as claimed in claim 8, characterized in that said material (16) has a comparatively high reflectivity to radiation with a wavelength in the range from 320 to 400 nm.

* * * * *